United States Patent [19]
Le et al.

[11] Patent Number: 5,220,089
[45] Date of Patent: Jun. 15, 1993

[54] OLEFIN UPGRADING BY SELECTIVE CATALYSIS

[75] Inventors: Quang N. Le, Cherry Hill; Robert T. Thomson, Voorhees, both of N.J.

[73] Assignee: Mobil Oil Corporation, Fairfax, Va.

[21] Appl. No.: 718,887

[22] Filed: Jun. 21, 1991

[51] Int. Cl.$^5$ ............................ C07C 4/06; C07C 6/04
[52] U.S. Cl. ................................... 585/643; 585/649; 585/653
[58] Field of Search ............... 585/649, 653, 708, 643

[56] References Cited

U.S. PATENT DOCUMENTS

| | | | |
|---|---|---|---|
| 4,439,409 | 3/1984 | Puppe et al. | 502/60 |
| 4,570,026 | 2/1986 | Keyworth et al. | 585/649 |
| 4,929,793 | 5/1990 | Morrison | 585/708 |
| 4,956,514 | 9/1990 | Chu | 585/533 |
| 4,969,987 | 11/1990 | Le et al. | 585/649 |
| 5,026,936 | 6/1991 | Leyshon et al. | 585/653 |

Primary Examiner—Anthony McFarlane
Attorney, Agent, or Firm—Alexander J. McKillop; Malcom D. Keen; L. G. Wise

[57] ABSTRACT

Olefins are converted to lower alkene hydrocarbon products, e.g., propene, butenes, and isoalkenes with zeolite MCM-22 catalyst. This catalytic conversion is particularly useful in the selective separation of linear olefins in mixed hydrocarbon streams, employing MCM-22 catalyst to convert these straight-chain unsaturated components to lighter products, particularly, $C_3$-$C_4$ olefins. One potential application of this selective separation is in the removal of linear olefins from FCC gasoline.

32 Claims, No Drawings

OLEFIN UPGRADING BY SELECTIVE CATALYSIS

BACKGROUND OF THE INVENTION

This invention relates to a process for converting intermediate olefins, e.g., $C_5$–$C_{12}$ linear mono-alkenes, in contact with a shape selective porous zeolite catalyst to provide lower olefins and isoalkene hydrocarbon products, especially propene, butenes and $C_4$–$C_5$ tertiary alkenes.

In view of phasing out of leaded gasoline and restrictions on the aromatics content of gasoline fuels, there is a great impetus for developing processes which upgrade olefins to high octane components. One such class of materials is aliphatic tertiary ethers, such as methyl tert-butyl ether (MTBE) and tert-amyl methyl ether (TAME). However, the availability of isobutylene and isoamylene feedstock for these ethers is limited. Therefore, processes for making these olefins from readily available feedstocks are sought. The process described herein is one such process and involves the conversion of readily available refinery feedstock, such as olefinic gasoline, to products rich in lower olefins, such as isobutylene and isoamylene.

The ability of shape selective zeolites such as ZSM-5 to convert olefins has been recognized previously. Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

Recent developments in zeolite catalysts and hydrocarbon conversion processes have created interest in utilizing olefinic feedstocks, such as petroleum refinery streams rich in olefins, for the production of $C_4^+$ tertiary olefins. The $C_5$–$C_7$ light naptha range product of FCC operations is very rich in normal and branched mono-alkenes.

It has been discovered that a new zeolite, designated MCM-22, is an effective catalyst for converting these intermediate olefins to propene and lower isoalkenes at high selectivity.

SUMMARY OF THE INVENTION

An improved process has been found for upgrading olefinic feedstock to iso-alkene rich product by shape selective catalysis at elevated temperature and low pressure. The improvement herein comprises selectively reacting linear olefins in a mixed olefinic feedstock containing branched components in contact with MCM-22 zeolite catalyst under reaction conditions sufficient to yield propene, isobutene and isopentene.

A selective alkene disproportionation process has been discovered wherein a mixture of intermediate molecular weight monoalkenes comprising at least one linear ethylenically unsaturated component and at least one branched alkene component is contacted under interconversion conditions with acid metallosilicate catalyst having the structure of MCM-22 zeolite.

DESCRIPTION OF SPECIFIC EMBODIMENTS

In shape selective zeolite catalysis, at low pressure and high temperature light and intermediate olefins can be interconverted or redistributed to produce olefinic product rich in isoalkenes.

In the process for catalytic conversion of olefins using an acid crystalline zeolite, such as ZSM-5 type catalyst, process conditions can be varied to favor the formation of either gasoline, distillate, lube range products. In the "MOG/D" process disclosed by C. T-S Chu in U.S. patent application Ser. No. 07/461,896, light olefins are oligomerized to high molecular weight distillate range olefins over shape selective MCM-22. In such processes using shape selective zeolite catalysts the olefin molecular weight growth to heavier hycrocarbons proceeds through a sequence of oligomerization and cracking reactions thermodynamically forced at relatively high pressures of about 5600 kPa (800 psia) and relatively low temperatures.

At much lower pressure and higher temperature up to about 700° C., thermodynamics restrict the olefin distribution to low molecular weight. This is the basis for the olefin interconversion process, i.e., to operate under conditions where linear olefins, such as $C_5$–$C_{12}$ mono-alkenes, can be converted selectively to an equilibrated distribution of olefins with iso-butenes and iso-pentenes maximized.

Many olefins are suitable for use as feedstock in the process of this invention, especially linear monoalkenes having 5 to 12 carbon atoms. Suitable olefinic feedstocks can be obtained from a variety of sources including fossil fuel processing streams such as fluid catalyst cracking (FCC) of heavy hydrocarbons, coal by-products, and various synthetic fuel processing streams. Olefinic effluent from the fluidized catalytic cracking of gas oil, and the like, is a valuable source of mixed linear and branched olefins, mainly $C_5$–$C_{12}$ olefins, suitable for conversion according to the present olefin interconversion process. Olefinic refinery streams can be advantageously converted to valuable higher hydrocarbons employing the catalytic interconversion process of this invention.

The olefin interconversion process as utilized in the present invention can use fixed bed, moving bed or fluid bed reactors containing MCM-22 zeolite catalyst or mixtures thereof with other shape selective catalysts, such as ZSM-5. Typical operating conditions encompass temperatures between 300° and 550° C., low pressure, generally between 100 and 1000 kPa, and high space velocity. Catalyst acidity can also be a factor in the reaction. It is preferred to maintain the acid activity (alpha value) of MCM-22 in the range of about 1 to 150, preferably less than 50, and most preferably less than 10.

Olefin upgrading has been improved by use of new MCM-22 zeolite as a catalyst for interconversion of olefin, such as n-pentenes, n-hexenes, etc. to higher value products, viz., isobutylene and isoamylenes. MCM-22 olefin interconversion catalysis is also characterized by low yields of undesirable normal C3–C5 alkanes. The process is preferably carried out at relatively low pressure (less than about 700 kpa) and high temperature (typically greater than about 300° C.) to maximize $C_4$+$C_5$ tertiary olefin yields. While the process can be carried out in either a fixed or a fluid-bed mode, the latter is preferred due to the relatively rapid catalyst aging.

DESCRIPTION OF ZEOLITE CATALYSTS

Careful selection of catalyst components to optimize C3–C4 and isoalkene selectivity is important to overall success of the process. The catalyst may consist essentially of MCM-22 aluminosilicate zeolite, having an acid cracking activity less than 15 (standard alpha value) and moderately low constraint index (C.I.=1.5). The moderately constrained medium pore zeolite has a pore size of about 5–8A°, able to accept linear olefin components found in most FCC naphtha may be used, it is advantageous to employ standard MCM-22, suitably modified if desired to adjust acidity. A typical zeolite catalyst component having Bronsted acid sites may consist essentially of aluminosilicate zeolite with 5 to 95 wt. % silica and/or alumina binder.

Usually the zeolite crystals have a crystal size from about 0.01 to 2 microns or more. In order to obtain the desired particle size for fluidization in the turbulent regime, the zeolite catalyst crystals are bound with a suitable inorganic oxide, such as silica, alumina, etc. to provide a zeolite concentration of about 5 to 95 wt %.

In selective olefin disproportionation reactions, it is advantageous to employ a standard zeolite having a silica:alumina molar ratio of 25:1 or greater in a once-through fluidized bed unit to convert about 5 to 50 weight percent, preferably about 10–30 wt %, of the C5–C12 feedstock hydrocarbons in a single pass. Particle size distribution can be a significant factor in transport fluidization and in achieving overall homogeneity in dense bed, turbulent regime or transport fluidization. It is desired to operate the process with particles that will mix well throughout the bed. It is advantageous to employ a particle size range consisting essentially of 1 to 150 microns. Average particle size is usually about 20 to 100 microns.

In the present invention MCM-22, a new zeolite which has been found to be active for a wide variety of hydrocarbon conversions, is shown to have high activity and selectivity for the selective conversion of naphtha-range olefinic C5–C12 hydrocarbons to higher value C3–C5 linear and iso-olefins.

The synthetic porous crystalline material employed as catalyst in the selective cracking of this invention, referred to herein as "zeolite MCM-22" or simply "MCM-22", appears to be related to the composition named "PSH-3" described in U.S. Pat. No. 4,439,409. Zeolite MCM-22 does not appear to contain all the components apparently present in the PSH-3 compositions. Zeolite MCM-22 is not contaminated with other crystal structures, such as ZSM-12 or ZSM-5, and exhibits unusual sorption capacities and unique catalytic utility when compared to the PSH-3 compositions synthesized in accordance with U.S. Pat. No. 4,439,409. The entire contents of U.S. Pat. No. 4,954,325 (Rubin et al) and applications Serial Nos. 07/254,524; 07/98,176; and 07/890,268 are incorporated herein by reference.

The synthetic porous crystalline material employed as catalyst in the olefin oligomerization process of this invention, referred to herein as "zeolite MCM-22" or simply "MCM-22", appears to be related to the composition named "PSH-3" described in U.S. Pat. No. 4,439,409. Zeolite MCM-22 does not appear to contain all the components apparently present in the PSH-3 compositions. Zeolite MCM-22 is not contaminated with other crystal structures, such as ZSM-12 or ZSM-5, and exhibits unusual sorption capacities and unique catalytic utility when compared to the PSH-3 compositions synthesized in accordance with U.S. Pat. No. 4,439,409.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$(0.005-0.1)Na_2O:(1-4)R:X_2O_3:nYO_2;$ wherein R is an organic component. The Na and R components are associated with the zeolite as a result of their presence during crystallization, and are easily removed by post-crystallization methods hereinafter more particularly described.

Zeolite MCM-22 is thermally stable and exhibits high surface area greater than 400 m$^2$/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations. It can, therefore, be used as an olefin interconversion catalyst with acid activity without an exchange step. To the extent desired, however, the original sodium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the activity of the catalyst for olefin interconversion. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in Table I below:

TABLE I

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE II

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |

TABLE II-continued

| Interplanar d-Spacing (A) | Relative Intensity, I/Io × 100 |
|---|---|
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/I$_o$, where I$_o$ is the intensity of the strongest line or peak, and d (obs.) the interplanar spacing in Angstroms Units (A), corresponding to the recorded lines, were determined. In Tables I and II, the relative intensities are given in terms of the symbols W=weak, M=medium, S=strong and VS=very strong. In terms of intensities, these may be generally designated as follows:

W=0-20

M=20-40

S=40-60

VS=60-100

It should be understood that these X-ray diffraction patterns are characteristic of all species of the present crystalline composition. The sodium form as well as other cationic forms reveal substantially the same pattern with some minor shifts in interplanar spacing and variation in relative intensity. Other minor variations can occur depending on the Y to X, e.g., silicon to aluminum, mole ratio of the particular sample, as well as its degree of thermal treatment.

Prior to its use as olefin interconversion catalyst, the MCM-22 crystals should be subjected to thermal treatment to remove part or all of any organic constituent present therein. Zeolite MCM-22, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the olefin interconversion process of this invention, the zeolite MCM-22 crystals should be dehydrated, at least partially. This can be done by heating the crystals to a temperature in the range of from about 200° C. to about 595° C. in an inert atmosphere, such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
| --- | --- | --- |
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered. The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The MCM-22 crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the MCM-22 crystalline material with another material which is resistant to the temperatures and other conditions employed in the olefin interconversion process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with zeolite MCM-22, i.e., combined therewith or present during its synthesis, which itself is catalytically active may change the conversion and/or selectivity of the catalyst. Inactive materials suitably serve as diluents to control the amount of conversion so that the higher value olefin products can be obtained economically and orderly without employing other means for controlling the rate of reaction. These materials may be incorporated into naturally occurring clays, e.g., bentonite and kaolin, to improve the crush strength of the catalyst under commercial olefin oligomerization operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with MCM-22 crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with zeolite MCM-22 also include inorganic oxides, notably alumina.

In addition to the foregoing materials, the MCM-22 crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the catalyst of this invention may be increased by steaming. U.S. Pat. Nos. 4,663,492; 4,594,146; 4,522,929; and 4,429,176, the entire disclosures of which are incorporated herein by reference, describe conditions for the steam stabilization of zeolite catalysts which can be utilized to steam-stabilize the catalyst for use herein. The steam stabilization conditions include contacting the catalyst with, e.g., 5–100% steam at a temperature of at least about 300° C. (e.g., 300°–650° C.) for at least one hour (e.g., 1–200 hours) at a pressure of 101–2,500 kPa. In a more particular embodiment, the catalyst can be made to undergo steaming with 75–100% steam at 315°–500° C. and atmospheric pressure for 2–25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same, or even lower than, the Alpha Value of the unsteamed catalyst. Steaming therefore provides an appropriate method for the modification of the acid activity of the catalyst and is suitable for reducing the acid activity to desired levels in the conventional manner. The acid activity of the catalyst may also be reduced by cation exchange with cations of an alkali metal such as sodium or potassium, either alone or in combination with steaming.

The selective olefin conversion process of the present invention can be suitably carried out by contacting the olefinic feed with zeolite MCM-22 catalyst under moderate olefin conversion conditions, e.g., a temperature of from about 300° to about 550° C., preferably from about 400° to about 450° C., a pressure of from 100 to about 1000 kPa, preferably from about 150 to about 500 kPa and at space velocity (WHSV) of from about 0.1 to about 100 $hr^{-1}$, preferably from about 0.2 to about 20 $hr^{-1}$.

In order to more fully illustrate the olefin conversion process of this invention and the manner of practicing same, the following examples are presented. In examples illustrative of the synthesis of zeolite MCM-22, whenever sorption data are set forth for comparison of sorptive capacities for water, cyclohexane and/or n-hexane, they were Equilibrium Adsorption values determined as follows:

A weighed sample of the calcined absorbent was contacted with the desired pure absorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the MCM-22 crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22 and are preferred for the zeolite component of catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 $sec^{-1}$). The Alpha Test is described in U.S. Pat. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*. Vol. 61, p. 395.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

$SiO_2/Al_2O_3 = 30.0$ $OH^-/SiO_2 = 0.18$ $H_2O/SiO_2 = 44.9$ $Na/SiO_2 = 0.18$ $R/SiO_2 = 0.35$ where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table III. The sorption capacities of the calcined material were measured to be:

$H_2O$ 15.2 wt. %

Cyclohexane 14.6 wt. % n-Hexane 16.7 wt. % The surface area of the calcined crystalline material was measured to be 494 $m^2/g$.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio = | 21.1 |

TABLE III

| Degrees 2-Theta | Interplanar d-Spacing (A) | $I/I_o$ |
|---|---|---|
| 2.80 | 31.55 | 25 |
| 4.02 | 21.98 | 10 |
| 7.10 | 12.45 | 96 |
| 7.95 | 11.12 | 47 |

TABLE III-continued

| Degrees 2-Theta | Interplanar d-Spacing (A) | I/I$_o$ |
|---|---|---|
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.17 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table IV. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table IV. The sorption and surface area measurements were of the calcined product.

TABLE IV

| Example | 3 | 4 | 5 |
|---|---|---|---|
| Synthesis Mixture, mole ratios | | | |
| SiO$_2$/Al$_2$O$_3$ | 30.0 | 30.0 | 30.0 |
| OH$^-$/SiO$_2$ | 0.18 | 0.18 | 0.18 |
| H$_2$O/SiO$_2$ | 19.4 | 19.4 | 44.9 |
| Na/SiO$_2$ | 0.18 | 0.18 | 0.18 |
| R/SiO$_2$ | 0.35 | 0.35 | 0.35 |
| Product Composition, Wt. % | | | |
| SiO$_2$ | 64.3 | 68.5 | 74.5 |
| Al$_2$O$_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| SiO$_2$/Al$_2$O$_3$, mole ratio | 22.5 | 20.9 | 26.0 |
| Adsorption, Wt. % | | | |
| H$_2$O | 14.9 | 13.6 | 14.6 |
| Cyclohexane | 12.5 | 12.2 | 13.6 |
| n-Hexane | 14.6 | 16.2 | 19.0 |
| Surface Area, m$^2$/g | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of H$_2$O. To the combined solution were added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table V:

TABLE V

| Product Composition (uncalcined) | |
|---|---|
| C | 12.1 wt. % |
| N | 1.98 wt. % |
| Na | 640 ppm |
| Al$_2$O$_3$ | 5.0 wt. % |
| SiO$_2$ | 74.9 wt. % |
| SiO$_2$/Al$_2$O$_3$, mole ratio | 25.4 |
| Adsorption. wt. % | |
| Cyclohexane | 9.1 |
| N-Hexane | 14.9 |
| H$_2$O | 16.8 |
| Surface Area, m$^2$/g | 479 |

EXAMPLE 8

Twenty-five grams of solid crystal product from Example 7 were calcined in a flowing nitrogen atmospheres at 538° C. for 5 hours, followed by purging with 5% oxygen gas (balance N$_2$) for another 16 hours at 538° C.

Individual 3 g samples of the Calcined material were ion-exchanged with 100 ml of 0.1 N TEABr, TPABr and LaCl$_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| | Exchange Ions | | |
|---|---|---|---|
| Ionic Composition, wt. % | TEA | TPA | La |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite has very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

$SiO_2/B_2O_3 = 6.1$ $OH^-/SiO_2 = 0.06$ $H_2O/SiO_2 = 19.0$ $K/SiO_2 = 0.06$ $R/SiO_2 = 0.30$ where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| | |
|---|---|
| $H_2O$ (12 Torr) | 11.7 wt. % |
| Cyclohexane (40 Torr) | 7.5 wt. % |
| n-Hexane (40 Torr) | 11.4 wt. % |

The surface area of the calcined crystalline material was measured (BET) to be 405 m²/g.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = | 1406 |
| $SiO_2/(Al + B)_2O_3$, molar ratio = | 25.8 |

EXAMPLE 12

A portion of the calcined crystalline product of Example 11 was treated with $NH_4Cl$ and again calcined. The final crystalline product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

$SiO_2/B_2O_3 = 12.3$ $OH^-/SiO_2 = 0.056$ $H_2O/SiO_2 = 18.6$ $K/SiO_2 = 0.056$ $R/SiO_2 = 0.30$ where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ (12 Torr) | 14.4 wt. % |
| Cyclohexane (40 Torr) | 4.6 wt. % |
| n-Hexane (40 Torr) | 14.0 wt. % |

The surface area of the calcined crystalline material was measured to be 438 m²/g.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio = | 249 |
| $SiO_2/(Al + B)_2O_3$, molar ratio = | 28.2 |

EXAMPLE 14

A portion of the calcined crystalline product of Example 13 was tested in the Alpha Test and found to have an Alpha Value of 5.

EXAMPLE 15

Another zeolite MCM-22 sample was prepared by adding 4.49 parts quantity of hexamethyleneimine to a mixture containing 1.00 part sodium aluminate, 1.00 part 50% NaOH, 8.54 parts Ultrasil VN3 and 44.19 parts deionized $H_2O$. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized $H_2O$ and dried. The zeolite was then calcined in nitrogen at 540° C., exchanged with an aqueous solution of ammonium nitrate and calcined in air at 540° C. The zeolite was tabletted, crushed and sized to 30/40 mesh.

The MCM-22 catalyst had the following properties:

| | |
|---|---|
| Surface Area (BET), m²/g | 503 |
| $SiO_2/Al_2O_3$ (molar) | 27 |
| Na, ppm | 495 |
| Alpha | 693 |

| Sorption Properties, wt. % | |
|---|---|
| $H_2O$ | 15.0 |
| $CyC_6$ | 12.5 |
| $n-C_6$ | 16.0 |
| Ash at 1000° C., wt. % | 99.05 |

Process Example A—Selective olefin conversion reactions are demonstrated to show selectivity in producing lower olefins and isoalkenes. This example of FCC gasoline cracking is performed in a nontransport regime fluid bed reactor using steamed MCM-22/silica-alumina clay catalyst (25 wt % zeolite, 4 alpha), prepared according to Example 15 In the reactor, catalyst is heated to 425° C. under nitrogen and maintained at this temperature and 200 kPa (15 psig) for one hour. To commence the reaction, light FCC gasoline ($C_5$-102° C.) is charged to the reactor at a rate of 1.7 parts by weight feed/part total catalyst-hour ( 6.8 WHSV). Nitrogen is cofed to the reactor to insure proper fluidization of the catalyst in the turbulent regime. Feedstock is fed to the reactor for 3 hours, followed by 60 minutes of nitrogen stripping. The entire reactor effluent from the feed and stripping periods is collected and analyzed by gas chromatography.

The results from studies of FCC gasoline cracking over MCM-22, displayed in Table A, show that over 60% of the linear isomers in the feedstream are converted to lighter products, which are primarily $C_3$-$C_4$ olefins. The selective nature of the linear olefin cracking is evident since the conversion levels for all other $C_5+$ components are significantly lower.

TABLE A

The Cracking of Light FCC Gasoline To Light Olefins over MCM-22

| Composition, wt % | Feed | Product | Net Conv. |
|---|---|---|---|
| Light Gas ($C_1$-$C_2$) | 0.0 | 1.0 | |
| $C_3$-$C_4$ Paraffins | 1.6 | 4.6 | |
| $C_3$-$C_4$ Olefins | 3.1 | 17.6 | |
| $C_5$-$C_6$ Paraffins | 26.7 | 25.7 | 3.7% |
| Linear $C_5$-$C_6$ Olefins | 14.1 | 5.6 | 60.3% |
| Branched $C_5$-$C_6$ Olefins | 20.7 | 16.8 | 18.8% |
| Other $C_6$ (Cyclics, etc.) | 8.7 | 6.9 | 20.7% |
| Total $C_7+$ | 25.2 | 22.1 | 12.3% |

The reaction effluent may be separated to recover an olefinic product stream rich in $C_4$-$C_5$ tertiary olefins, which may be converted to MTBE and/or TAME; and wherein a $C_6+$ heavy hydrocarbon is recovered to recycle for further conversion. It is also feasible to recover propene and butenes as a product stream, with a $C_5+$ stream rich in tertiary olefins being partially etherified as a gasoline blending component. It is understood that unreacted branched aliphatics in the feedstock enhance the octane value of the gasoline for blending.

In addition to the above reaction run, the selective removal of linear olefins in hydrocarbon streams may potentially be performed in many other reactor configurations; however, fluidized bed configuration is preferred, particularly at high temperature (350°-550° C.) and short-contact time (<10 sec) conditions. Moving-bed and fixed-bed reactors are also viable for high activity and stable catalysts which might not require frequent regeneration. Prefered process conditions for fixed and moving -bed configuration would be in lower reactor temperature, space velocities (1-10 WHSV) and in the substantial absense of added hydrogen.

In addition to FCC gasolines, other potential olefinic feedstocks include coker naphtha, dehydrogenated naphtha, dehydrogenated Udex raffinate, and olefin oligomers. Typical olefinic feedstock materials for selective upgrading are produced in petroleum refineries by distillation of FCC reaction effluent. Typical FCC naphtha feedstock usually contain 15 to 50 wt. % $C_5$-$C_{12}$ normal and branched alkanes, $C_6+$ cycloaliphatic (i.e., naphthene) hydrocarbons, and 1 to 40% aromatics. The $C_5$-$C_{12}$ hydrocarbons have a normal boiling range up to 175° C. In addition to FCC naphtha, the process can utilize various feedstocks, such as derived from hydrocracking, heavy FCC naphtha, hydrocracked naphtha, coker naphtha, visbreaker naphtha and mixtures thereof. For purposes of explaining the invention, discussion is directly mainly to FCC light naphtha materials.

The selective cracking of linear olefins over MCM-22 may provide an attractive route for the upgrading of hydrocarbon streams, including FCC gasoline. The light hydrocarbon products (propylene and butenes) as well as unreacted $C_5+$ branched olefins can be used as feedstocks for the production of "clean fuels" such as ethers and alkylate.

If proposed regulations on the minimum oxygen content and maximum olefin concentration in the gasoline pool are mandated, it would be desirable to preferentially remove the linear olefins from FCC gasoline and thus increase the concentration of unconverted branched olefins, which may be recovered from reaction effluent and converted to ethers. The production of $C_4-$ olefins from the cracking reaction is an additional benefit since these hydrocarbons are used in downstream processes, such as alkylation and etherification, to produce other "clean fuel" components.

Selective removal of linear olefins from mixed hydrocarbon streams has many potential applications, including the production of "clean fuels." The catalytic cracking of gas oil (FCC) produces, among other products, large volumes of gasoline-range hydrocarbons. However, for environmental reasons, replacement of the highly olefinic FCC product with high octane ethers and alkylate in the gasoline pool would be highly desirable. Since these latter components are produced from feedstocks such as propylene, butenes, and branched $C_5$-$C_7$ olefins, it would be beneficial to selectively crack linear olefins in FCC gasoline to $C_3$-$C_4$ olefinic products. Therefore, development of a process to accomplish this selective conversion would be highly desirable.

The cracking of FCC gasoline would be performed in a reactor located downstream of the FCC unit. The $C_4-$ product stream from the gasoline cracking process could be sent to the FCC unsaturated gas plant, with branched $C_5+$ olefins possibly being etherified with methanol to increase the oxygen content of the gasoline pool.

Various modifications can be made to the system, especially in the choice of equipment and non-critical processing steps. While the invention has been described by specific examples, there is no intent to limit the inventive concept as set forth in the following claims.

We claim:

1. A process for selectively converting $C_5+$ linear olefin feedstock containing branched olefin to produce a reaction effluent containing propene and butenes, which comprises contacting said feedstock with an olefin interconversion catalyst composition in a catalytic reaction zone under selective linear olefin interconversion conditions, said catalyst comprising a synthetic porous crystalline material characterized by an X-ray diffraction pattern including values substantially as set forth in Table I of the specification.

2. The process of claim 1 wherein the synthetic porous crystalline material is characterized by an X-ray diffraction pattern including values substantially as set forth in Table II of the specification.

3. The process of claim 1 wherein the synthetic porous crystalline material has a composition comprising the molar relationship $$X_2O_3:(n)YO_2,$$

wherein n is at least about 10, X is a trivalent element and Y is a tetravalent element.

4. The process of claim 2 wherein the synthetic porous crystalline material has a composition comprising the molar relationship:

$$X_2O_3:(n)YO_2,$$

wherein n is at least about 10, X is a trivalent element and Y is a tetravalent element.

5. The process of claim 1 wherein the synthetic porous crystalline material possesses equilibrium adsorption capacities of greater than about 4.5 wt. % for cyclohexane vapor and greater than about 10 wt. % for n-hexane vapor.

6. The process of claim 3 wherein X is selected from the group consisting of aluminum, boron, gallium and combinations thereof and Y is selected from the group consisting of silicon, germanium and combinations thereof.

7. The process of claim 3 wherein X is selected from boron or aluminum and Y is selected from silicon.

8. The process of claim 1 wherein said synthetic porous crystalline material has been treated to replace original cations, at least in part, with a cation or mixture of cations selected from the group consisting of hydrogen and hydrogen precursors.

9. The process of claim 4 wherein X is selected from the group consisting of aluminum, boron, gallium and combinations thereof and Y is selected from the group consisting of silicon, germanium and combinations thereof.

10. The process of claim 4 wherein X consists essentially of boron and Y consists essentially of silicon.

11. The process of claim 2 wherein said synthetic porous crystalline material contains original cations and said porous crystalline material has been treated to replace said original cations, at least in part, with a cation or mixture of cations selected from the group consisting of hydrogen and hydrogen precursors.

12. The process of claim 1 wherein said synthetic porous crystalline material has been thermally treated at a temperature up to about 925° C. in the presence or absence of steam.

13. The process of claim 8 wherein said synthetic porous crystalline material has been thermally treated at a temperature up to about 925° C. in the presence or absence of steam.

14. The process of claim 11 wherein said synthetic porous crystalline material has been thermally treated at a temperature up to about 925° C. in the presence or absence of steam.

15. The process of claim 1 wherein said synthetic porous crystalline material is combined with a material matrix.

16. The process of claim 15 wherein said matrix material is a silica or alumina-containing material.

17. The process of claim 15 wherein the catalyst is provided in the form of extrudate, beads or fluidizable microspheres.

18. The process of claim 1 wherein the olefin has 5 to 12 carbon atoms.

19. The process of claim 1 wherein the reaction conditions include a temperature greater than 300° C., a pressure less than 1000 kpa and weight hourly space velocity of about 0.1 to 100 $hr^{-1}$.

20. The process of claim 1 wherein the reaction conditions include a temperature of from about 300 to 550° C. a pressure of about 100 to 1500 kpa and weight hourly space velocity of 0.2 to 20 $hr^{-1}$.

21. The process of claim 1 wherein reaction effluent is separated to recover an olefinic product stream rich in $C_4$-$C_5$ tertiary olefins and wherein a $C_6+$ heavy hydrocarbon is recovered to recycle for further conversion.

22. The process of claim 1 wherein the olefin feed comprises propylene; wherein said reaction effluent comprises iso-alkene rich product containing isobutylene and isoamylene.

23. The process of claim 1 wherein the catalyst consists essentially of borosilicate MCM-22 having an alpha value acid activity less than 10, based on active catalyst solids.

24. The process of claim 1 wherein the catalyst consists essentially of zeolite MCM-22 having an alpha value acid activity of 0.1 to 150, based on active catalyst solids.

25. The process of claim 1 wherein the catalyst consists essentially of zeolite MCM-22 having an alpha value acid activity of 0.1 to 50, based on active catalyst solids.

26. The process of claim 1 wherein the catalyst consists essentially of zeolite MCM-22 having an alpha value acid activity of 0.1 to 10, based on active catalyst solids.

27. The process of claim 1 wherein the olefin feed comprises a mixture of substantially linear and branched $C_5$-$C_{12}$ olefins; and wherein hydrogen is added to the olefin feed.

28. The process of claim 1 wherein $C_5+$ product fraction is rich in branched mono-olefins.

29. The process of claim 1 wherein said feedstock is partially converted and wherein at least a portion of unreacted feedstock is separated as a gasoline product stream from $C_4$-$C_5$ hydrocarbons and light gas.

30. In a process for upgrading linear and branched $C_5$-$C_{12}$ olefin feedstock to iso-alkene rich product by shape selective catalysis at elevated temperature and low pressure, the improvement which comprises: reacting the olefin feedstock in contact with MCM-22 zeolite catalyst under reaction conditions sufficient to provide increased yield of isobutene and isopentene.

31. A selective alkene disproportionation process wherein a mixture of monoalkenes comprising at least one linear ethylenically unsaturated component and at least one tertiary alkene component is contacted under interconversion conditions with acid metallosilicate catalyst having the structure of MCM-22 zeolite, wherein selective interconversion of the linear unsaturated component produces lower alkenes without substantial reaction of said tertiary alkene component.

32. The process of claim 31 wherein said interconversion conditions comprise reaction temperatures in the range of about 300° C. to 550° C. and pressure in the range of 100 kpa to 1000 kpa.

* * * * *